United States Patent [19]

Cohen

[11] Patent Number: 5,503,561
[45] Date of Patent: Apr. 2, 1996

[54] BELIEF-SCAN FALLACY FINDER COMPUTERIZED FALLACY DETECTION AND DIAGNOSTIC SYSTEM

[76] Inventor: Elliot D. Cohen, 2601 SE. Solana La., Port St. Lucie, Fla. 34952

[21] Appl. No.: 198,999

[22] Filed: Feb. 18, 1994

[51] Int. Cl.$^6$ ....................................................... G09B 7/00
[52] U.S. Cl. .......................... 434/236; 434/237; 434/238; 434/322; 434/323
[58] Field of Search ................................. 434/236–238, 434/307 R, 322, 323, 327, 335

[56] References Cited

U.S. PATENT DOCUMENTS

| | | | |
|---|---|---|---|
| 4,820,167 | 4/1989 | Nobles et al. | 434/307 R X |
| 4,829,431 | 5/1989 | Ott et al. | 434/323 |
| 4,863,384 | 9/1989 | Slade | 434/236 X |
| 4,895,518 | 6/1990 | Arnold et al. | 434/236 X |

Primary Examiner—Richard J. Apley
Assistant Examiner—Glenn E. Richman

[57] ABSTRACT

A computerized system consisting of 10 interfacing modules is disclosed capable of detecting common thinking errors known as fallacies. An operator enters sentences referencing their own beliefs, or someone else's. Utilizing analysis options through which further modules are accessed, the system scans entry data searching for substrings associated with specific fallacies. Operators are frequently asked yes or no questions to check further for these fallacies. Counters in scanning routines limit program redundancy and records each of the scanning modules to keep track of detected fallacies so that results can be summarized and evaluated. Beeping twice when fallacies are detected the system presents on a monitor screen, or other output device, the names of fallacies committed, the sentences in which they have occurred, brief explanations, suggestions for avoiding these fallacies, and, if requested, definitions of them. In the system's summarizing and evaluating stage, it lists and classifies all fallacies detected; describes general problems and tendencies inherent in the proffered thinking; and issues cautions and recommendations.

14 Claims, 8 Drawing Sheets

FIG. 1
MODULE 1

FIG. 1B
MODULE INTERFACES

FIG. 2 BASIC DESIGN OF FALLACY SCANNING PROCESS IN MODULES 2 THRU 9

FIG. 2A
BASIC DESIGN OF FALLACY SCANNING PROCESS IN MODULES 2 THRU 9 (CONT'D)

FIG. 3B
MESSAGES IN THE EVALUATION PROCESS

BELIEF-SCAN FALLACY FINDER COMPUTERIZED FALLACY DETECTION AND DIAGNOSTIC SYSTEM

FIELD OF THE INVENTION

This invention relates to checking one's own thinking or the thinking of others and, in particular, to a computerized detection for determining irrational or illogical beliefs known as fallacies.

BACKGROUND OF THE INVENTION

The present invention is directed to an inexpensive method for checking one's own thinking or the thinking of others for irrational or illogical beliefs known as fallacies. While computerized testing systems exist such as U.S. Pat. No. 4,895,518, no such computerized fallacy detection and diagnostic system is known in the art.

Current art requires those seeking relief from problems of anger, guilt, stress and interpersonal relationships to seek counseling in order to correct common thinking errors. Self-diagnosis is not usually feasible because of the extensive amount of information needed to accurately do so as well as the difficulty of maintaining an objective stance. In addition, while some self-help books discuss certain fallacies, it is still left to readers to properly and objectively apply these discussions to their own particular cases.

A counselor trained in the area of cognitive therapy may be able to work with the individual in an effort to correct faulty thinking. Counselors, however, may themselves lack the ability to detect common thinking errors due to lack of training or experience in this area. In these cases the individual is likely to receive inadequate treatment.

Owing to the high cost of counseling for the average consumer as well as the discouragement of unsuccessful treatment, a second consultation is not likely to be sought. In other cases people's problems may not appear to them to be serious enough to warrant the high cost of therapy so that these problems will go untreated.

Thus what is needed in the art is a tool which can operate as an inexpensive adjunct to available counseling options for said individual as well as professional uses; this tool having a form of artificial intelligence in order to detect and diagnose common fallacies that disrupt a person's thinking.

SUMMARY OF THE INVENTION

BELIEF-SCAN FALLACY FINDER detects at least 46 common thinking errors known as fallacies. These individual fallacies are classified under five different types: Evaluative, Factual, Logical, Relevance, and Meaning. For example, Evaluative Fallacies involve misuses of value language and are often involved in emotional stress, including anger, guilt, anxiety and depression.

When operators type in ordinary language sentences referencing their own thinking on any subject, or the thinking of another person, BELIEF-SCAN checks these sentences for possible fallacies. The operator may choose to scan for all fallacy types which yields a "Complete Analysis" or for selected types. The program poses yes or no questions called "Inquiries," the answers to which help to locate possible fallacies.

When fallacy-specific criteria have been satisfied, BELIEF-SCAN beeps two times alerting the operator about a fallacy. On a monitor screen or other output device, it presents the name of the fallacy, the sentence in which the fallacy has been detected, a brief rationale for why the thinking is faulty, a suggestion for avoiding the given fallacy; and it provides access to a definition.

Since there is often probability and not certainty that a given fallacy has been committed, BELIEF-SCAN often qualifies its fallacy findings with the word "possible" or "likely". However, such judgments are not returned unless the possibility that the fallacy was committed is a reasonable one based on operator-provided information.

After scanning for fallacies is completed, BELIEF-SCAN provides a "Summary of Possible Fallacies Found" and, when indicated, gives an "Overall Evaluation" of general thinking problems based on the type and frequency of fallacies listed in the summary. This evaluation includes a definition of the problem, problem indications, and general recommendations for remedying the problem. It may also include specific cautions and a description of the subject's tendency to commit a specific fallacy type.

The program works on the principle that the specific fallacies scanned for are a function of certain linguistic expressions consisting of words or phrases. When these key linguistic expressions are found within the entered data, the basis for exposing the correlated fallacy is set. At this juncture, relevant questions are often posed in order to further specify word usage, the speaker's motives, and other information that may be directly relevant to the determination of whether the fallacy in question has been committed.

An objective of the extant invention is to serve as an adjunct to cognitive psychotherapy, where exposure of irrational thinking is primary. It can be used to detect and diagnose irrational cognitions having negative effects on assertiveness, decision-making, the emotions, and interpersonal relations; for individual as well as professional use.

Still another objective is for use as a teaching aid in critical thinking courses in high schools, community colleges and universities. It can also serve within the context of education to help students check their essays and writing assignments for irrational claims much as they now use spell-checkers for the purposes of checking for misspellings.

Yet still another objective of the invention is for use in employee training and management programs for improving proficiency and productivity in the work place, including the ability to manage tress by detecting and helping to reduce employee thinking errors.

DETAILED DESCRIPTION OF THE INVENTION

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed environment.

Figure 1:
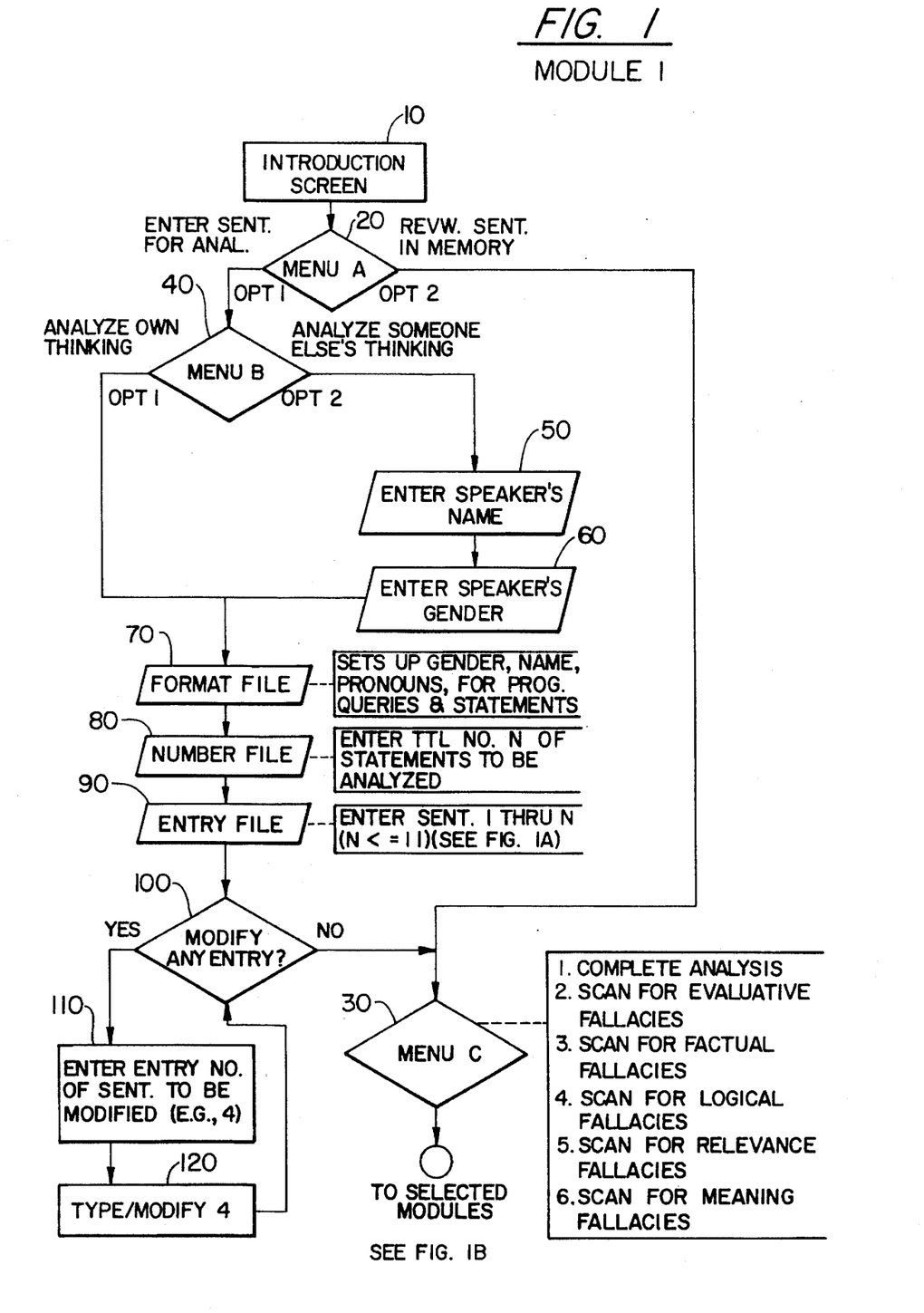
FIG. 1 is a flow chart of Module 1, the module containing output data files defining the nature and form of the subsequent analysis.

Regarding FIG. 1, after BELIEF-SCAN is booted on a conventional personal computer having a display screen and keyboard input, by typing the word "belief", an introduction screen 10 welcomes the operator to BELIEF-SCAN and provides a brief, general description of the system.

The operator accesses 20 Menu A which contains two options: A1. Enter Sentences for Analysis and A2. Review Sentences in Memory. The desired option is accessed by entering either 1 or 2.

Option A2 is used only if sentences remain in memory from a previous program run. When this option is selected, Menu C 30 provides 6 different program options located in a Fallacy selection area: C1. Complete Analysis to Scan for all types of fallacies; C2. Scan for Evaluative Fallacies which are misuses of evaluative, emotional language; C3. Scan for Factual Fallacies which are distortions of facts or their probabilities; C4. Scan for Logical Fallacies which are faulty reasoning patterns; C5. Scan for Relevance Fallacies which are appeals to unrelated information; C6. Scan for Meaning Fallacies which are misleading or unclear word usages. The operator can select any of these 6 options by entering the desired option number (see FIG. 1B, step 230).

Selection of Option A1 of Menu A presents Menu B 40. This menu provides two options: B1. Analyze Own Thinking, B2. Analyze Someone Else's Thinking. Option B2 50 requires the speaker's name, i.e. the name of the person whose beliefs are being analyzed; and speaker's gender 60 from among the following options: 1. male, 2. female, 3 not known. When the appropriate gender number is entered, the program defines variables for the speaker's name and gender 70 in a format selection area. For example, if option 1 is selected then let X$= "himself" and if the name entered is "John," then let S$= "John". This name and gender information is stored in said output Format File and used in subsequent modules to make statements and to ask questions about the speaker's thinking.

When Option B1 of Menu B is selected 40, the program defines variables 70 in terms appropriate to discussing the operators own thinking. For example, let X$="yourself" and let Z$="you". This information is then stored in said output Format File for use in subsequent modules.

At step 80, the operator enter up to 11 sentences to be analyzed with 255 spaces allowed for each sentence, and in which "a sentence" may consist of several grammatical sentences. The number entered 80 is stored in a Number selection area that controls variables in the Entry File 90, later used in order to find fallacies. The number entered in step 80 is also used to control the number of sentences the program permits the operator to enter for analysis (see FIG. 1A).

All general information needed to run the program is complete upon the aforementioned steps allowing the analyzing of sentences by typing each sentence at each number prompt. At step 90, each sentence is stored in a separate string variable in the Entry selection area. This entry process is shown in detail in FIG. 1A.

When all sentences for analysis are entered, they are displayed on the screen and consecutively numbered. In the present embodiment of this invention, a maximum of four sentences per screen are displayed and subsequent numbers are accessed by pressing ENTER. At step 100, the operator is asked if any of these sentences need to be modified or changed. If the answer to this question is "Yes" then the operator 110 enters the number of the sentence to be modified. When this number is entered the screen displays 120 the sentence to be modified. Above the sentence is the prompt to type/modify the sentence that is displayed. When the operator retypes the sentence at the current cursor location and presses ENTER, the screen is cleared and the corrected sentence is now displayed along with the other consecutively numbered sentences previously displayed. The program returns to step 100 and the operator is again asked if he/she wants to modify any entry. This loop continues until the operator says "No" to any modifications. When the operator selects the latter option, Menu C appears as in step 30, and is accordingly asked to select one of the six analysis options from this menu.

Figure 1A:
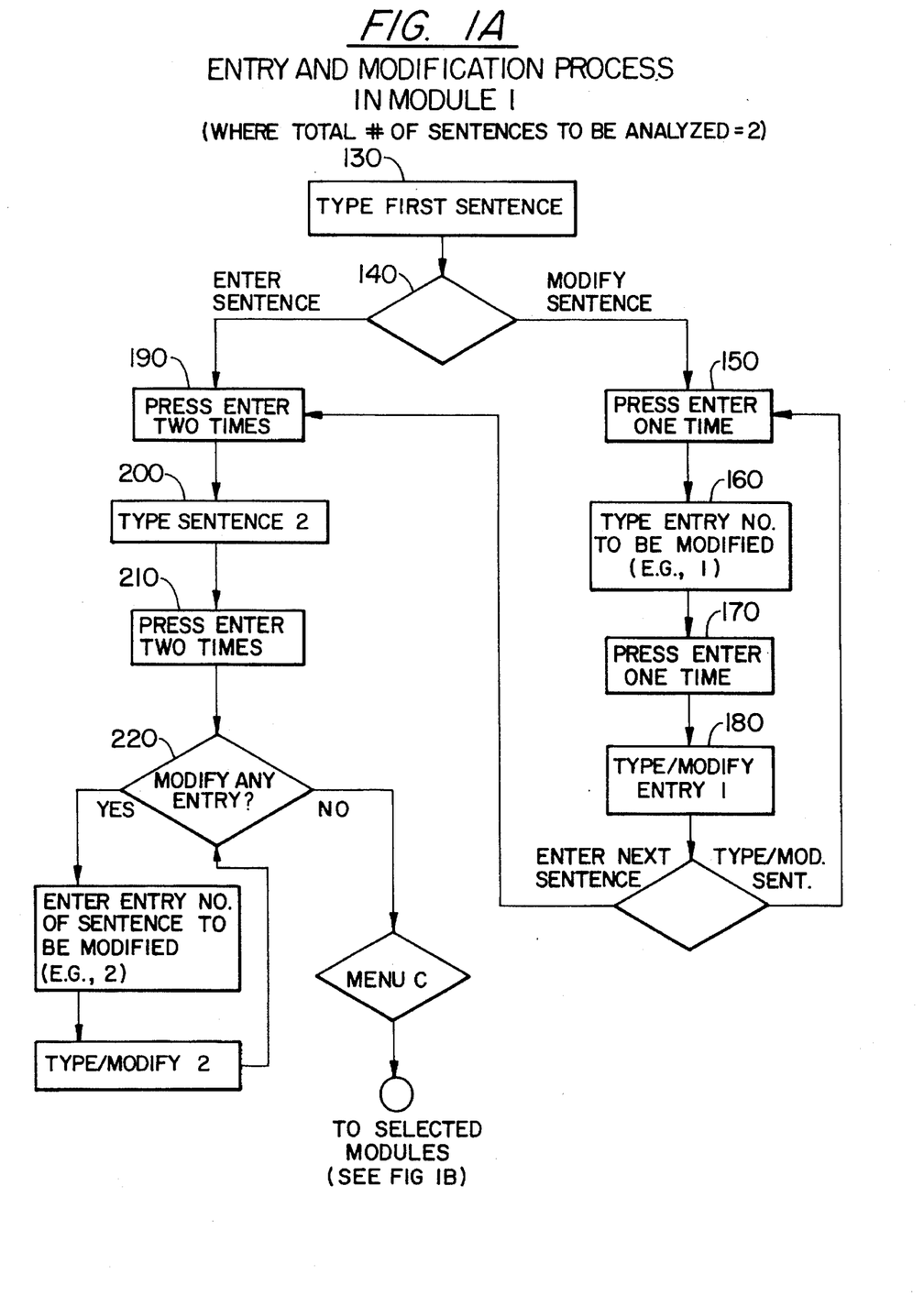
FIG. 1A is a flow chart of the entry and modification process in Module 1 where, as an example, 2 sentences have been entered for analysis.

FIG. 1A illustrates the process of entry and modification in Module 1 where the total number of sentences N to be analyzed as per the number entered in the Number File (FIG. 1, step 80) is 2. The process is the same, however, when N<>2.

After typing a sentence 130 the operator can either enter the next sentence or modify any previous sentence 140. To modify a previous sentence, the operator must press ENTER one time at step 150; type at the current cursor position the number of the sentence to be modified at step 160; and press ENTER again at step 170. The sentence to be modified will appear on the screen. Above it will be the message to type/modify the sentence in question, for instance, "Type/Modify Entry 1" as shown in step 180. The cursor position will be below the sentence to be modified flush with the left screen margin. The operator must retype the sentence with the desired modifications and press ENTER. If the operator is to press enter a second time as indicated in step 190, the operator will be ready at step 200 to type the sentence with the next consecutive number, for instance "2" if the sentence just modified was "1". In this case, the number "(2)" will appear centered on the screen above the cursor which will be at the left screen margin.

To modify a further sentence instead of proceeding to enter a new sentence, the operator must repeat steps 150, 160, 170, and 180.

The operator can bypass the sentence with the next consecutive number and proceed to another number. For instance, if the operator modified sentence 1 and wants now to bypass sentence 2 and, instead, to enter sentence 3, the operator must enter "3" at step 160 and press ENTER at step 170. The message "Type/Modify 3" will appear on the screen and the operator can now proceed to make the third entry. On the other hand, if the operator has modified sentence 1 and presses ENTER a second time 190, the operator will be prompted at step 200 to type sentence 2. If the operator has, however, previously entered sentence 2 and had gone back to modify sentence 1, the operator is placed in the position of having to retype sentence 2. If the operator does not retype this sentence—underneath it at the current cursor position—and instead presses ENTER, the sentence will be erased from memory.

The operator can elect to make any desired modifications, if any, after completing the entry process. In this case, he or she must follow steps 130, 190, 200, and 210. When the total number N of sentences to be analyzed is reached, the program will, at step 220, automatically prompt the operator for any desired changes. This modification process is shown in FIG. 1A, steps 100, 110, and 120.

Figure 1B:
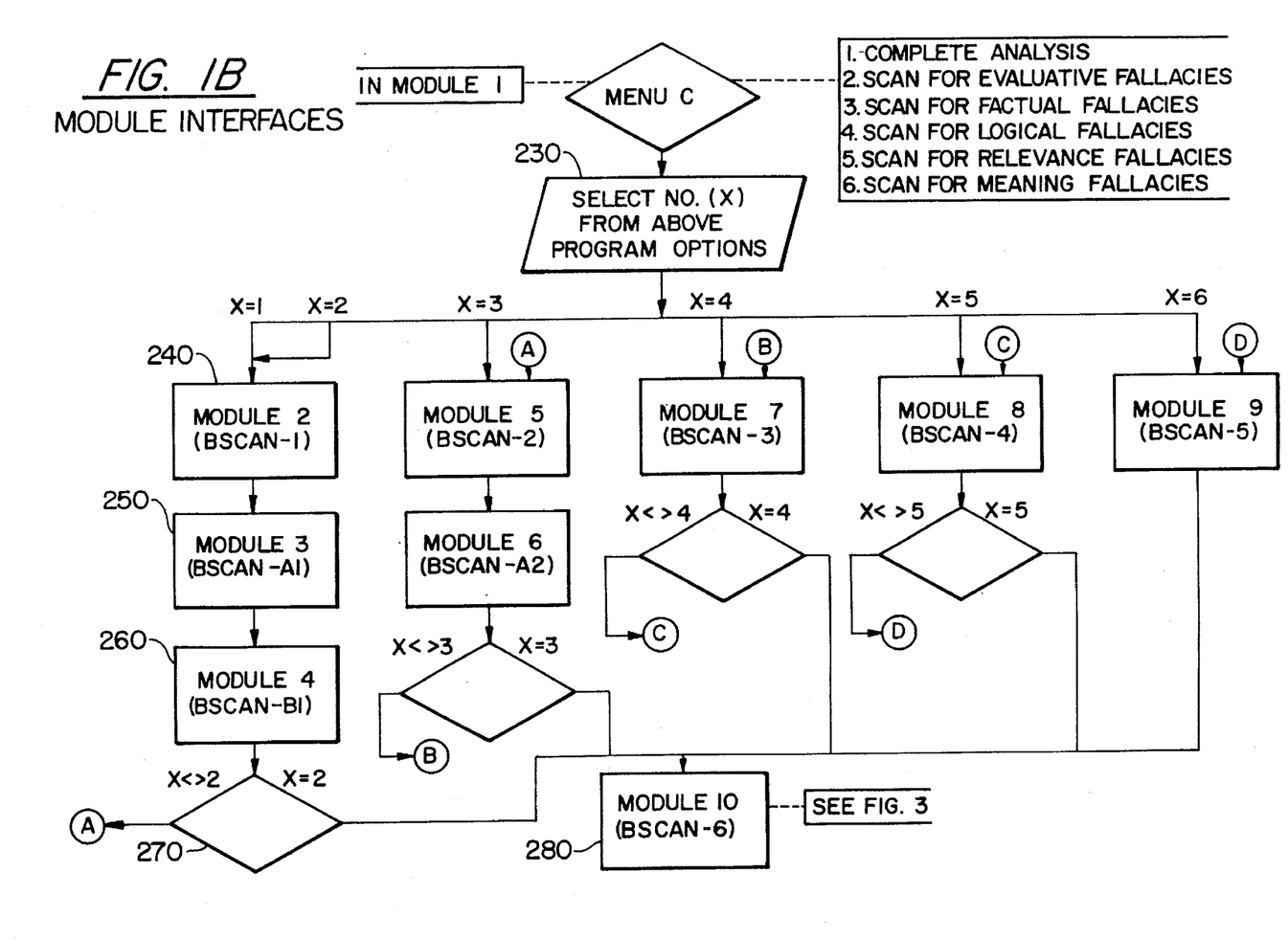
FIG. 1B is a flow chart of module interfaces between module 1 and all other subsequent modules in the program.

FIG. 1B shows the module interfaces for each of the program analysis options of Menu C. At step 230 the operator chooses the desired option number X from among the different program analysis options. This number is stored in an output file in Module 1, which is reopened for input in subsequent modules. This number is accordingly able to control chaining to program modules satisfying desired analysis options. For instance, X= 2 tells the program to Scan for Evaluative Fallacies, chaining to Module 2 through Module 4 as shown in steps 240, 250, and 260. Since Modules 2, 3, and 4 include program routines that specifically scan for evaluative fallacies, the desired analysis option, X= 2, is satisfied. The option number halts the chaining process from one module to the next, a process which would otherwise continue until each consecutively numbered module is run. This chaining process is halted at the juncture where all the modules satisfying the desired analysis option have been run. Where X= 2 at step 270, the linear chaining process is interrupted after all fallacy scanning routines are exhausted in Module 4. The X= 2 condition causes chaining to Module 10 to occur 280. The latter Module then summarizes and/or evaluates the fallacy search conducted in Modules 2 through 4 (see FIGS. 3 and 3A) in an antecedent selection area.

Figure 2:
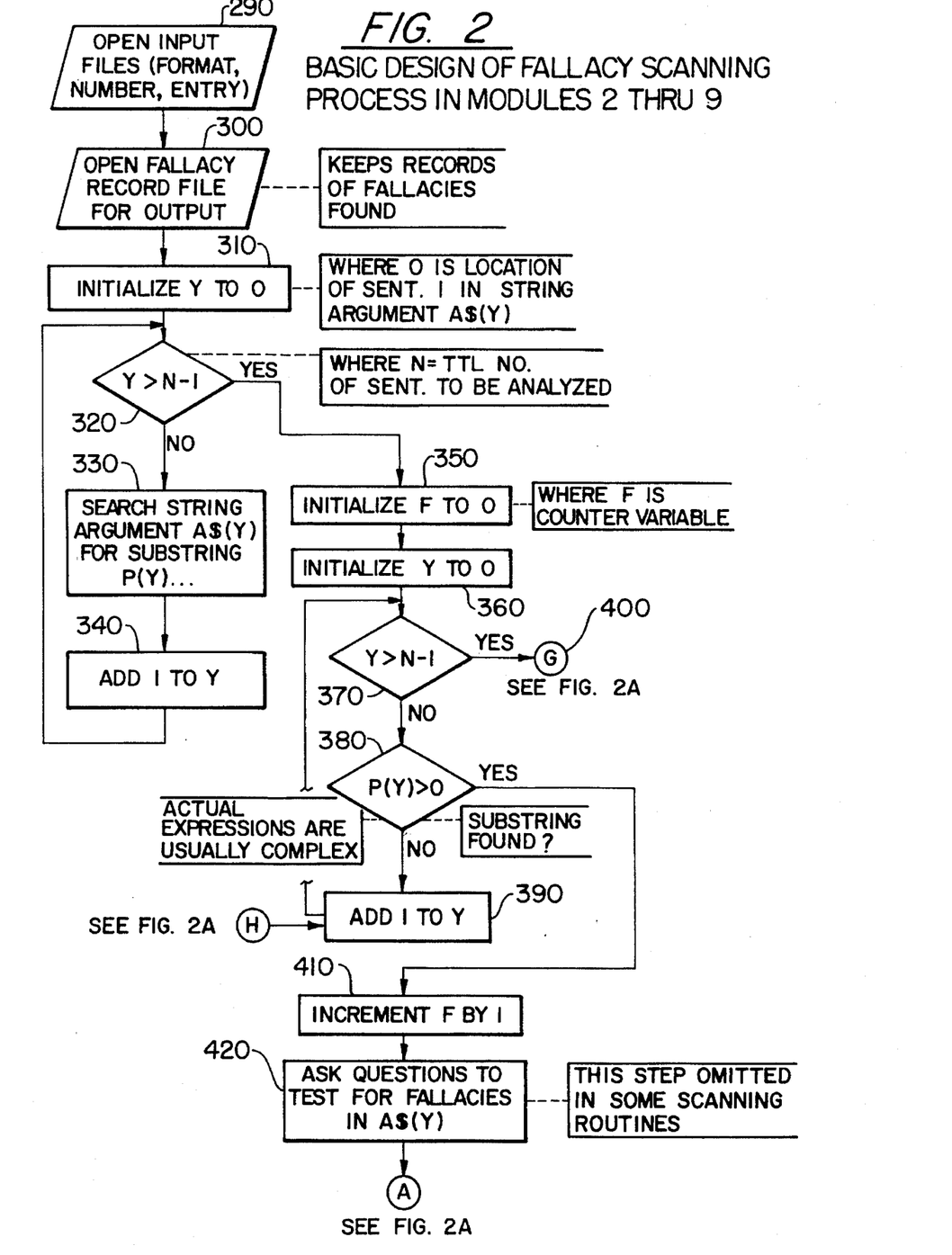
FIG. 2 is a flow chart depicting the basic design of the fallacy scanning process in Modules 2 through 9.

FIG. 2 illustrates the basic format of the fallacy scanning process used in Modules 2 through 9, which are the scanning modules. Each scanning module at 290 reopens the Format, Number and Entry Files for input, which files were opened for output as shown in FIG. 1, steps 70, 80, and 90, respectively.

Following step 290 is the opening at step 300 of an identification fallacy which is a record used to keep track of the fallacies that are found in the given scanning module. This Record File is itself reopened for input in Module 10 after completion of the scanning process, thereby serving to convey information required for summary and evaluation purposes (see FIG. 3, step 550).

At step 310, each element from 0 to 10 in the array A(Y) is respectively assigned to each of the string variables included in the Entry File (FIG. 1, step 90). Thus, for example, 0 is the location of sentence 1, 1 is the location of sentence 2, etc. At step 330, beginning with 0, the program then searches each sentence within these dimensions for a set of substrings P(Y) correlated to a given fallacy. To reduce unnecessary searching, however, the dimensions of the search are limited to N-1 where N is the total number of sentences to be analyzed as printed to the Number File. Since the element 0 in the array AS(Y) is used, 1 is subtracted from N. After each sentence is searched, 1 is added 340 to Y. When the condition Y> N-1 is satisfied, the loop terminates 320.

At step 350, a counter variable F is initialized to 0. This counter is needed to limit the amount of times the program will repeat the same routine thereby reducing program redundancy.

At step 360, Y is again initialized to 0 so that, starting with element 0 which contains sentence 1, BELIEFSCAN can read a series of conditional commands whose antecedents state that at least one instance of a substring within the searched set of substrings P(Y) has been found. If the antecedents are false 380, then 1 is added to Y 390 and the next sentence is scanned. If none of the antecedents are satisfied by any of the sentences submitted for analysis, so that at step 370 the condition Y> N-1 is true, then the program proceeds to the next scanning routine 400, scanning for further fallacies within the current scanning module, utilizing the same basic process described here. However, when an antecedent is true 380, the counter variable F is increased 410 by 1.

If the correlation between the substring in question and the commission of a given fallacy is significant enough to support a high probability that the fallacy has been committed, BELIEF-SCAN informs the operator. (See FIG. 2A, steps 440 and 450.) For example, the expression "makes me depressed" would support that the speaker is not recognizing any role his or her own cognitions might have played in the depression. A fallacy that is defined by such a lack of recognition would be indicated. (See source code included in detailed description of FIG. 2A)

In most cases, however, supplemental questions are needed in order to determine whether a fallacy is indicated. Thus, the program asks the operator such questions as may be needed to make this determination 420. For example, in a scanning routine that searches for stereotypes, the question may be asked, "Are you using the term blacks to refer to all or most of a certain race of people.

Figure 2A:
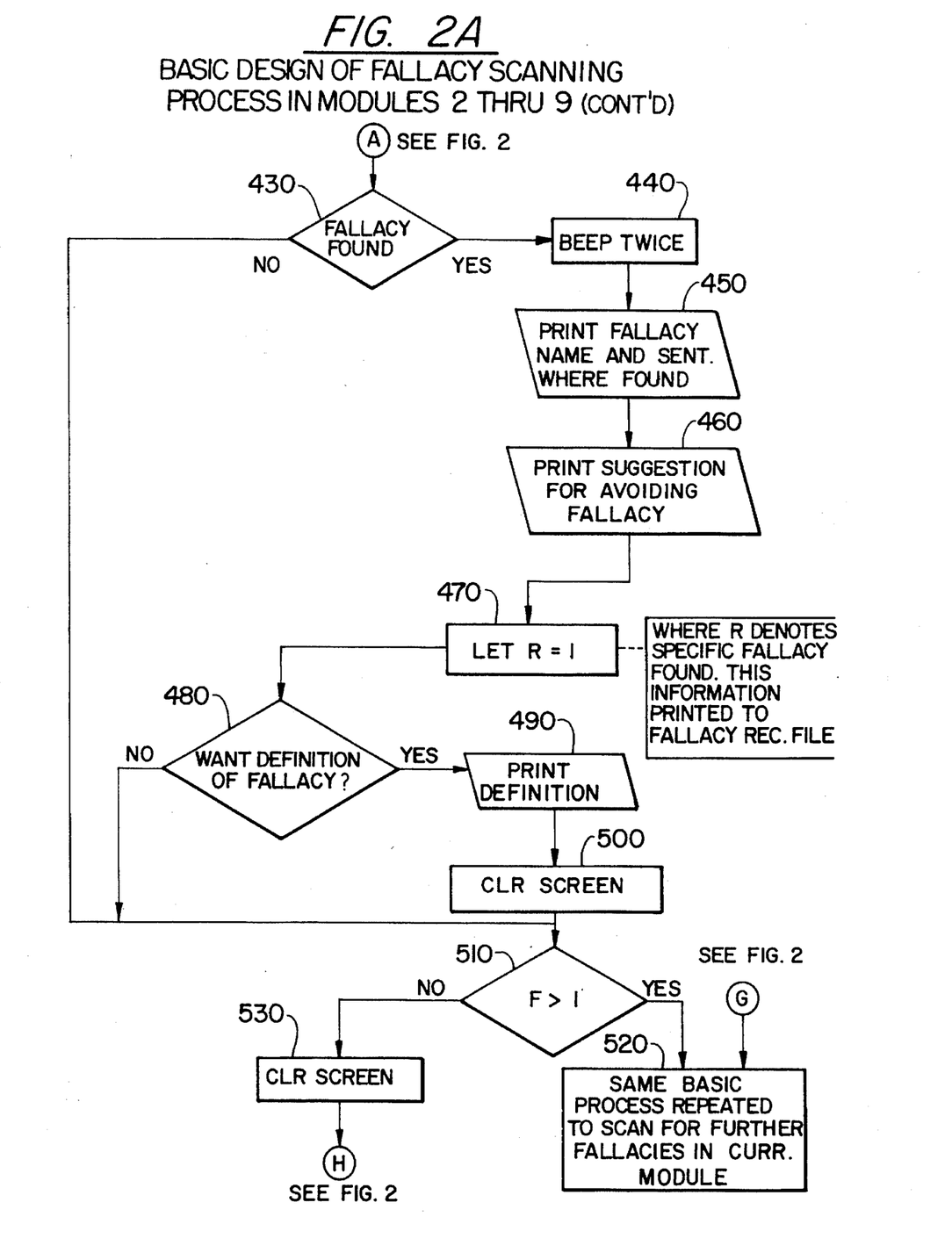
FIG. 2A is a continuation of the fallacy scanning process charted in FIG. 2.1.

Regarding FIG. 2A, when a fallacy is found 430, BELIEF-SCAN beeps two times 440 alerting the operator of the finding. The fallacy name and sentence in which the fallacy has been found appear on the screen 450. The program also provides a brief suggestion for avoiding the fallacy in the future 460.

At step 470 the value of 1 is assigned to the variable R, representing the specific fallacy found so that a record of the finding is established. This information is printed to the Record File shown in FIG. 2, step 300, which file is reopened in Module 10 ( see FIG. 3, step 550).

At step 480, the program asks operators if they want a definition of the specific fallacy that was found. If the operator says yes, then the definition appears on the screen 490. The operator is prompted to press ENTER and the screen is cleared 500. If the operator says no, then no definition is provided and the program proceeds to step 510.

At step 510, if the counter variable F is greater than 1, then the present routine is terminated and a new one is started 520. However, if F is not greater than 1, then the screen is cleared of any previous messages 530 and the program goes to the next Y (FIG. 2, step 390).

The following is a portion of source code illustrating key components of the fallacy scanning process in Modules 2 through 9:

```
101 For Y = 0 to N - 1
102    A(Y) = INSTR(A$(Y), "upsets me")
103    B(Y) = INSTR(A$(Y), "makes me depressed")
104 NEXT Y
105 LET F = 0
106 FOR Y = 0 to N - 1
107 IF A (Y) > 0 OR B (Y) > 0 THEN PRINT "'I Just
Can't Help This Feeling' Fallacy found in:";A$(Y) ELSE 120
108 PRINT
109 PRINT "Suggest taking responsibility for own feelings."
110 LET R = 1
```

```
-continued
111 PRINT
112 PRINT "Want definition of 'I Just Can't Help This Feeling'
Fallacy (YES = 1, NO = 0)?"
113 INPUT D
114 IF D = 0 THEN 118
115 PRINT "I JUST CAN'T HELP THIS FEELING =
Blaming your emotions entirely on external events without
acknowledging the role of your own thinking in causing those
emotions."
116 PRINT
117 PRINT "Press ENTER to continue"
118 CLS
119 IF F > 1 THEN GOTO 121 [REM new routine]
120 NEXT Y
```

Program source code often employs subroutines to accommodate information about fallacy findings, definitions of fallacies, and questions asked to determine whether fallacies have been committed. The set of substrings P(Y) that are searched often includes hundreds of instances. The conditionals, as for example in line 118, are therefore numerous and they are often logically complex having compound antecedents with conjunctive, disjunctive, and negative components.

Figure 3:
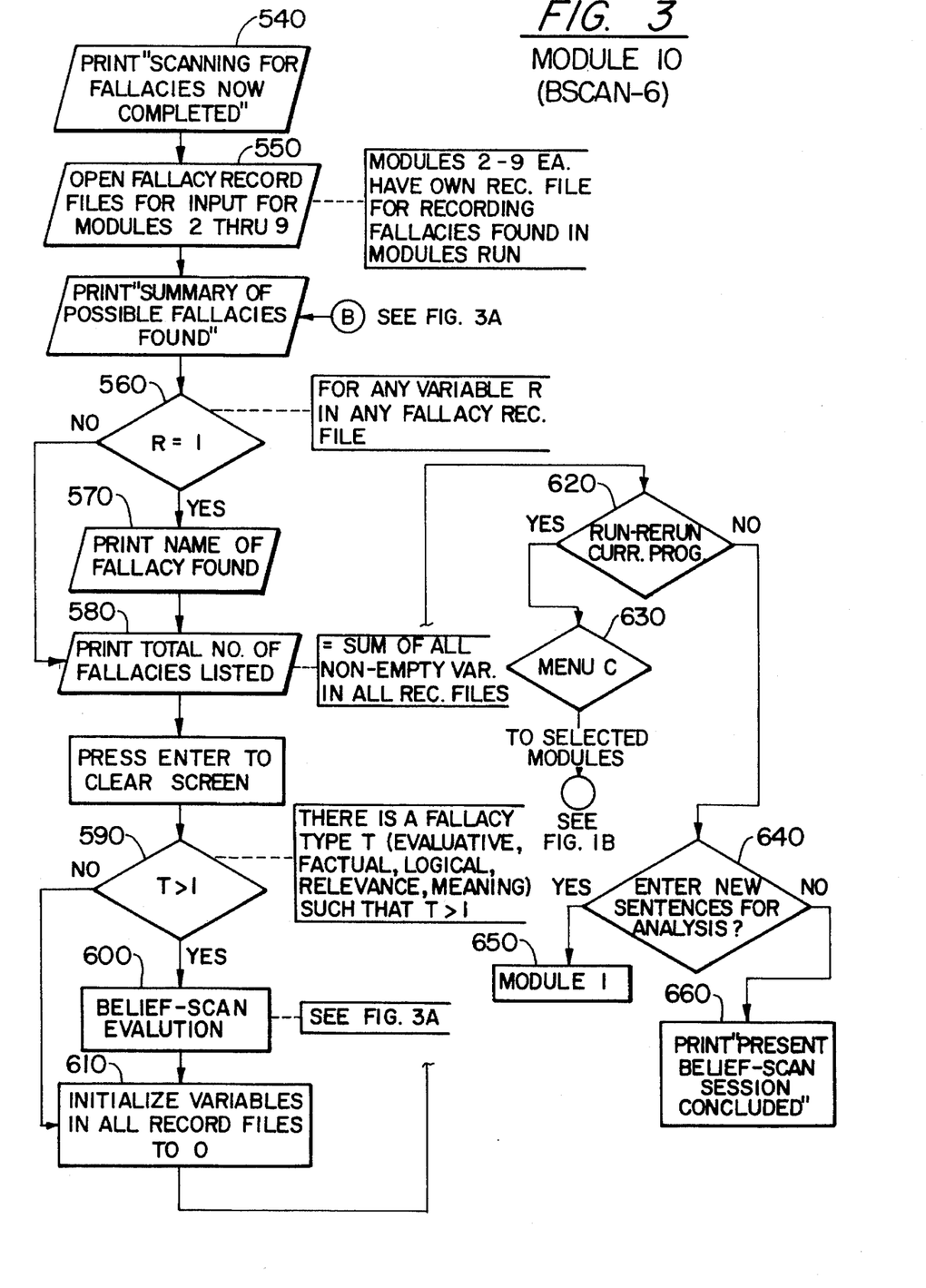
FIG. 3 is a flow chart of Module 10, the module that summarizes and evaluates results of the program analysis, and provides options for re-analyzing the same sentences or analyzing new sentences.

FIG. 3 shows the overview of Module 10. Upon completion of scanning, the program chains to this module. The opening message 540 appears on the screen, "Scanning for fallacies now completed."

The Fallacy Record Files are opened for input 550. Each of the scanning modules 2 through 9 has its own Record File. These files have kept a record of all possible fallacies found in the scanning process (see FIG. 2A, step 470).

Based on information provided in the Fallacy Record Files a "Summary of Possible Fallacies Found" is presented. That is, for any variable R in any Record File, if R=1 at step 560 then BELIEF-SCANprints the name of the possible fallacy found 570. Accordingly, this summary lists all fallacies that have been found in the scanning process. Each listing also includes the fallacy type in parentheses, e.g. "Stereotyping (Factual Fallacy)". This summary displays the number of fallacies listed 580, which is equal to the sum of the values of all Record Files. If this sum equals 0 then the program states that no fallacies were found.

At step 590, for any fallacy type T—Evaluative, Factual, Logical, Relevance, or Meaning—if the sum of the values of all type T variables as added from the Record Files is greater than 1, then BELIEF-SCAN clears the screen and provides an "Overall BELIEF-SCAN Evaluation" 600. (See FIG. 3A for evaluation process.)

At step 610, all variables in all Record Files are initialized to 0. This is necessary in order to clear memory of previous values so that these variables can be used to store new information in future program runs.

Alternatively, if it is false that T>1 at step 590, then all variables in all Record Files are directly initialized to 0 at step 610 and no evaluation is provided. This "threshold" condition of T>1 thereby permits evaluations to be provided if and only if there is a probability of a problem in need of evaluation.

Operators are asked if they want to run/rerun the current program 620. If an operator says yes, then Menu C appears 630 and the operator can re-select an option (see FIG. 1B, step 230). This enables the operator to subject the same sentences which are still in memory to further analysis or review.

If the operator says no 620, then BELIEF-SCAN will ask if the operator wants to enter new sentences for analysis 640. If the operator says yes to this latter question, then the program chains to Module 1 at step 650 so that new sentences can be entered. If the operator say no, then the message appears "Present BELIEF-SCAN Session Concluded" 660. While this is the end of the program, sentences remain in memory and can still be re-analyzed by re-booting the program and selecting Option 2A from Menu A (see FIG. 1, step 20).

Figure 3A:
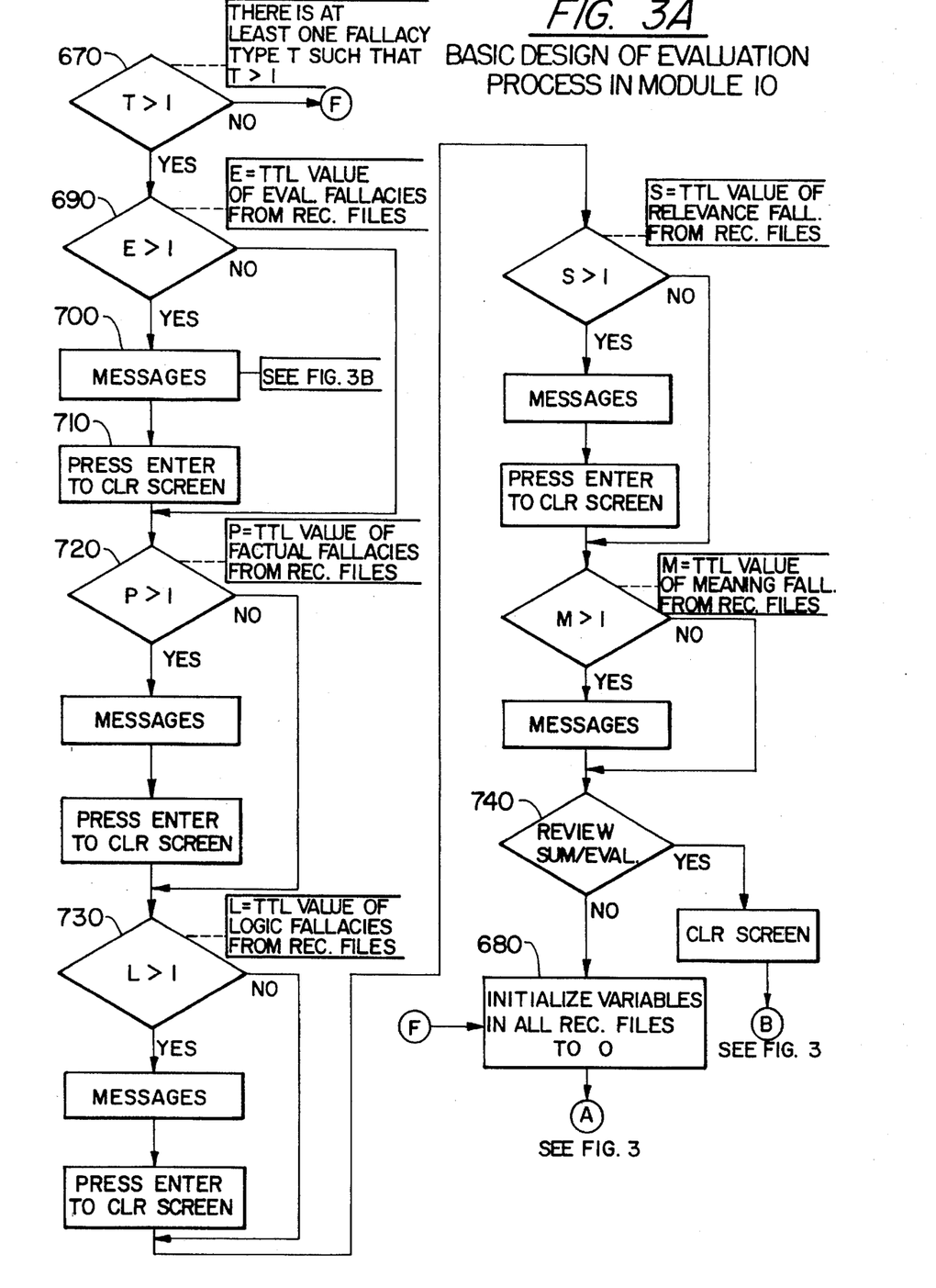
FIG. 3A is a flow chart depicting the basic design of the evaluation process in Module 10.

FIG. 3A illustrates the basic design of the evaluative process in Module 10. This evaluative process is engaged if, and only if, the "threshold" condition, T>1, is true 670 (see FIG. 3, step 590). If this condition is true, then the program goes on to step 690 and provides an overall evaluation. If it is false, then all variables in all Record Files are initialized to 0 at step 680.

At least 5 types of fallacies are detected by this invention: Evaluative, Factual, logical, Relevance, and Meaning. When two or more fallacies of the same type have been found, then BELIEF-SCAN generates specific evaluation messages associated with that fallacy type.

The program first looks in the Record Files for two or more Evaluative Fallacies 690. If this condition, referenced 690 as E>1, is true, then it generates specific messages associated with evaluative fallacies 700. The operator is then asked to press ENTER whereby the screen is cleared and the program looks in the Record Files for two or more of the next fallacy type 720, i.e. the Factual type.

If the program does not find two or more factual fallacies at step 720 so that the condition P>1 is false, then it directly searches Record Files of the next fallacy type 730. This process continues until all 5 fallacy types have been searched.

After all evaluation messages have been displayed, operators are asked if they want to review the Summary/Evaluation screens 740. If the operator says yes, then the program goes back to the Summary (see FIG. 3, steps 560, 570, and 580). If the operator says no, then the loop is terminated and the program proceeds to step 680 whereby all variables in all Record Files are initialized to 0.

Figure 3B:
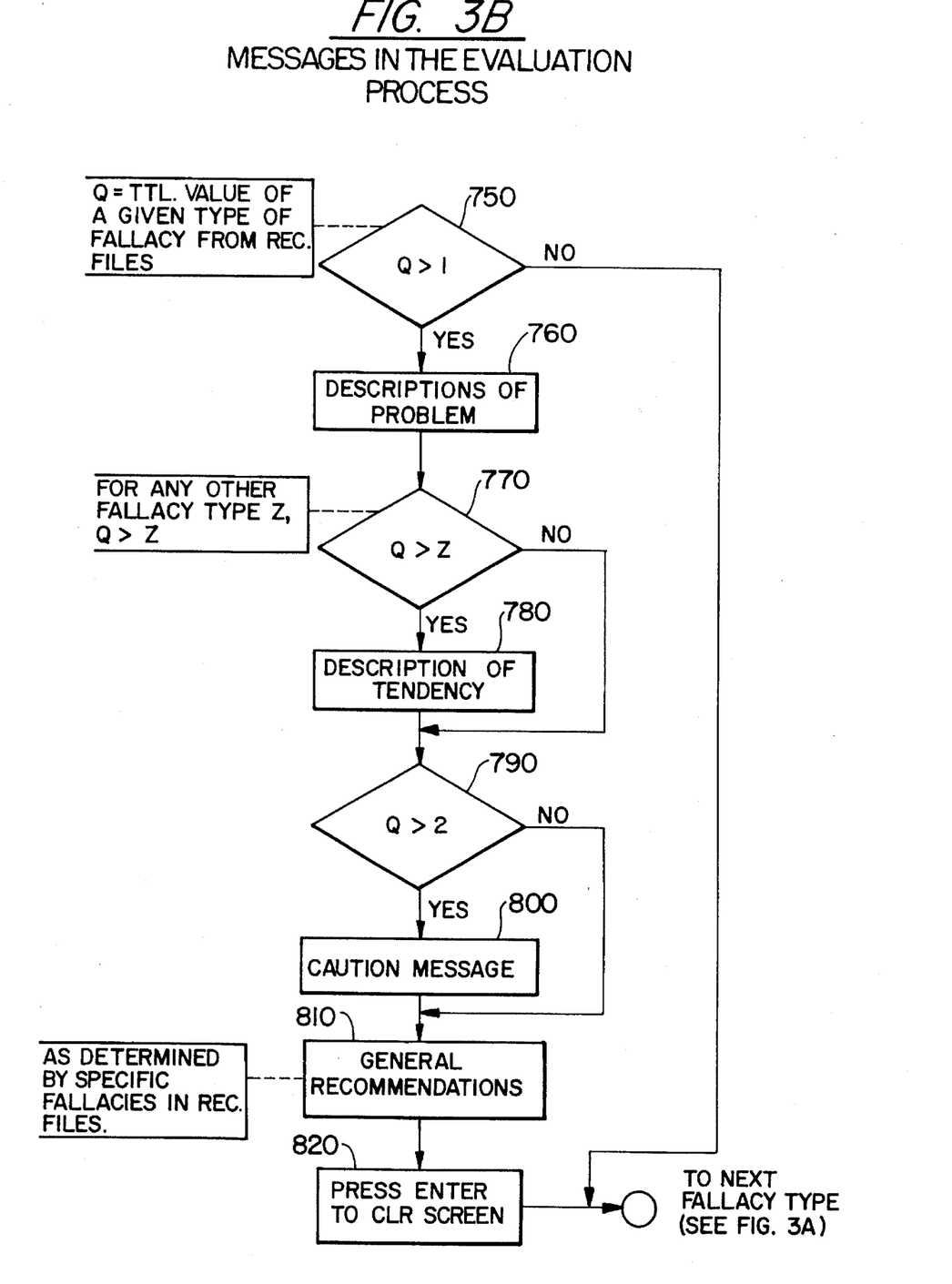
FIG. 3B is a flow chart showing the system of messages conveyed through the evaluation process in Module 10.

FIG. 3B shows the system of messages provided within the evaluation process of Module 10. If, as provided by the Record Files, the total value of a given fallacy type Q at step 750 is >1, then evaluation messages pertaining to Q are displayed.

Evaluation messages 760 include a description of a "Problem Indicated" as well as a description of what the problem is "Indicated by". For example, if the quantity of Factual Fallacies found were 2, then the evaluation would include the following messages:

PROBLEM INDICATED:

Unrealistic/distorted reality judgment.

INDICATED BY: Possible Factual Fallacies (Qty=2).

BELIEF-SCAN also informs the operator about any general "tendency" to commit a specific fallacy. If fallacy type Q is such that, for any other fallacy type Z that was scanned for, the condition Q>2 is true 770, then the program identifies a general tendency 780 to commit Q. For instance, if Evaluative Fallacies were more prevalent than any other type of fallacy, say 5 out of 7 fallacies found were Evaluative, then the following message would appear:

TENDENCY: 5 out of 7 of listed fallacies were Evaluative. This fallacy type was more prevalent than any other type.

Tendency messages are displayed only if the analysis option selected from Menu C is Option C1, that is, a complete analysis (See FIG. 1B.) Otherwise there can be no comparative basis from which to determine a tendency to commit one fallacy type more than any other.

BELIEF-SCAN evaluations may also include "Caution" messages. These messages are also a function of certain threshold conditions. That is, if for fallacy type Q, the condition Q>2 is true 790, then a "Caution" message is displayed 800. For example, 3 or more Evaluative Fallacies would cause the following message to be displayed:

CAUTION: Probable Emotional Stress.

If the condition of Q>2 is false 790, BELIEF-SCAN proceeds to step 810 wherein it displays "General Recommendations" for avoiding fallacies that have been recorded in the Record Files. Each recommendation that is displayed is thus a direct function of the specific instances of fallacy type Q that have been recorded. For example, a record of "Well Poisoning" in the Evaluative Fallacy Record File will cause the message:

GENERAL RECOMMENDATIONS: * Avoid intimidation/manipulation in relating/communicating with others.

When all recommendations have been displayed, the operator is prompted to press ENTER, whereby the screen is cleared 820 and the program searches Record Files for values> 1 of the next fallacy type.

It is to be understood that while I have illustrated and described certain forms of our invention, it is not to be limited to the specific forms or arrangement of components herein described and shown. It will be apparent to those skilled in the art that various changes may be made without departing from the scope of the invention and the invention is not to be considered limited to what is shown in the drawings and described in the specification.

What is claimed is:

1. A fallacy diagnostic detection method for use in conjunction with a computer comprising:

a display means;

microprocessor means; and means for entering data;

the method comprising the steps of:

first storing information for a contingent battery of questions in a format selection area;

second storing in a number selection area data corresponding to a quantity of statements to be analyzed based upon said information in a number selection area;

third storing said number selection of user-determined statements to be analyzed in an entry data selection area;

fourth storing a plurality of fallacy modules of said entry data selection area;

fifth storing in an antecedent selection area identification memory for identifying a plurality of fallacies is said end data selection area; and sixth storing an identification fallacy corresponding to at least one said fallacy as supported by said identification memory.

2. The method according to claim 1 wherein there is provided a further step of editing said entry selection area.

3. The method according to claim 1 wherein there is provided a further step of fallacy defining an identification fallacy according to said step of sixth storing.

4. The method according to claim 1 wherein there is provided a further step of identifying a fallacy in said entry, data selection area.

5. The method according to claim 1 wherein said fallacy modules include at least one evaluative fallacy.

6. The method according to claim 1 wherein said fallacy modules include at least one factual fallacy.

7. The method according to claim 1 wherein said fallacy modules include at least one logical fallacy.

8. The method according to claim 1 wherein said fallacy modules include at least one relevance fallacy.

9. The method according to claim 1 wherein said fallacy modules include at least one meaning fallacy.

10. The method according to claim 3 wherein there is provided a further step of summarizing recorded fallacies based upon said fallacy defining.

11. The method according to claim 10 wherein there is provided a further step of diagnosing thinking problems and tendencies based upon said summarizing.

12. The method according to claim 11 wherein there is provided a further step of recommending and cautioning based upon said diagnosing.

13. The method according to claim 1 wherein semantic content range of said statements to be analyzed includes all user determined selections according to said step of third storing.

14. The method according to claim 1 wherein there is provided a further step of reviewing analysis of said statements to be analyzed according to said step of third storing.

* * * * *

UNITED STATES PATENT AND TRADEMARK OFFICE
CERTIFICATE OF CORRECTION

PATENT NO. : 5,503,561
DATED     : April 2, 1996
INVENTOR(S) : Elliot D. Cohen

It is certified that error appears in the above-indentified patent and that said Letters Patent is hereby corrected as shown below:

```
Column 5, line 67, change "BELIEFSCAN" to -- BELIEF-SCAN--
Column 6, line 30, change "people." to --people?"--
Column 7, line 35, change "BELIEF-SCANprints" to
        --BELIEF-SCAN prints--
Column 10, lines 7-8, change "is said end" to
        --in said entry--
Column 10, line 18, delete comma after "entry"
```

Signed and Sealed this

Thirteenth Day of August, 1996

*Attest:*

BRUCE LEHMAN

*Attesting Officer*        *Commissioner of Patents and Trademarks*